(12) United States Patent
Rosser et al.

(10) Patent No.: US 11,051,777 B2
(45) Date of Patent: Jul. 6, 2021

(54) IMAGING NEUROLOGICAL DISEASE

(71) Applicant: GE Healthcare Limited, Buckinghamshire (GB)

(72) Inventors: Mark Rosser, Amersham (GB); Jan Wolber, Amersham (GB)

(73) Assignee: GE HEALTHCARE LIMITED, Buckinghamshire (GB)

(*) Notice: Subject to any disclaimer, the term of this patent is extended or adjusted under 35 U.S.C. 154(b) by 1001 days.

(21) Appl. No.: 14/907,428

(22) PCT Filed: Jul. 25, 2014

(86) PCT No.: PCT/EP2014/066042
§ 371 (c)(1),
(2) Date: Jan. 25, 2016

(87) PCT Pub. No.: WO2015/011267
PCT Pub. Date: Jan. 29, 2015

(65) Prior Publication Data
US 2016/0183897 A1 Jun. 30, 2016

(30) Foreign Application Priority Data
Jul. 25, 2013 (GB) .................. 1313291

(51) Int. Cl.
*A61B 6/00* (2006.01)
*A61K 51/04* (2006.01)
*A61B 6/02* (2006.01)
*G16H 50/20* (2018.01)

(52) U.S. Cl.
CPC ............ *A61B 6/481* (2013.01); *A61B 6/02* (2013.01); *A61B 6/501* (2013.01); *A61B 6/5217* (2013.01); *A61K 51/0455* (2013.01); *G16H 50/20* (2018.01)

(58) Field of Classification Search
None
See application file for complete search history.

(56) References Cited

PUBLICATIONS

Seibyl et al, "Decreased SPECT [123] B-CIT Striatal Uptake Correlates with Symptom Severity in Parkinson's disease", Annals of Neurology, vol. 38, No. 4, Oct. 1995.*
Wang et al. Comparison of the SERT-selective FPDB and VMAT2-slective radiotracers in a rat model of Parkinson's disease, Nucl. Med, Biol. 2010, B. 37, pp. 479-486.*
Japan Office Action corresponding to JP Application No. 2016-528546, dated Aug. 21, 2018.
Seibyl, J.P, et al., "Decreased Single-Photon Emission Computed Tomographic [1231]beta-CIT Striatal Uptake correlates with Symptom Severity in Parkinson's Disease", the American Neurological Association, 1995, vol. 38, Oct. 1995, pp. 589-598.

(Continued)

Primary Examiner — Amelie R Davis
Assistant Examiner — Marjan Saboktakin
(74) Attorney, Agent, or Firm — Jeff B. Vockrodt; Culhane Meadow, PLLC

(57) ABSTRACT

A method of imaging to permit calculation of left:right striatum uptake ratios is provided, and the degree of asymmetry used to assist in the diagnosis of neurological diseases. Also provided are a method of diagnosis, method of patient selection, and method of therapy monitoring using the imaging method, and software tools for use in the method.

16 Claims, 3 Drawing Sheets striatum R/L ratio

(56) References Cited

PUBLICATIONS

Hsiao, M., et al., "Dopamine transporter change in drug-naive schizophrenia: an imaging study with 99mTc-TRODAT-1", Schizophrenia Research 63, 2003, pp. 39-46.

Katzenschlager, R., et al., "[123I]-FP-CIT-SPECT Demostrates Dopaminergic Deficit in Orthostatic Tremor", Annals of Neurology, vol. 53, Apr. 2003, pp. 489-496.

Jacqueline A. Gleave et al., "Correlative single photon emission computed tomography imaging of [123I]altropane binding in the rat model of Parkinson's," Science Direct—Nuclear Medicine and Biology, 38 pp. 741-749, 2011.

Xiuying Cai et al., "Effects of levodopa on dopaminergic neurons and induced dyskinesia," Neural Regeneration Research, vol. 5, Issue 2, pp. 92-97, 2010.

Makoto Nakagawa et al., "PET evaluation of the relationship between D2 receptor binding and glucose metabolism in patients with parkinsonism," Original Article—Annals of Nuclear Medicine, vol. 19, No. 4, pp. 267-275, 2005.

M. Lauer et al., "Disturbed neural circuits in a subtype of chronic catatonic schizophrenia demonstrated by F-18-FDG-PET and F-18-DOPA-PET," Journal of Neural Transmission, 108, pp. 661-670, 2001.

A. Neumeister et al., "Dopamine transporter availability in symptomatic depressed patients with seasonal affective disorder and healthy controls," Psychological Medicine, vol. 31, Issue 08, pp. 1467-1473, 2001.

J. P. Seibyl et al., "Decreased Single-Photon Emission Computed Tomographic [123I]beta-CIT Striatal Uptake correlates with Sympton Severity in Parkinson's Disease," Annals of Neurology, vol. 38, No. 4, pp. 589-598, 1995.

Mei-Chun Hsiao et al., "Dopamine transporter change in drug-naive schizophrenia: an imaging study with 99mTc-TRODAT-1," Schizophrenia Research, vol. 65, Issue 1, pp. 39-46, 2003.

Regina Katzenschlager, MD, et al., "[123I]-FP-CIT-SPECT Demonstrates Dopaminergic Deficit in Orthostatic Tremor," Annals of Neurology, vol. 53, No. 4, pp. 489-496, 2003.

Yoshitaka Kumakura et al., "Elevated [18F]FDOPA utilization in the periaqueductal gray and medical nucleus accumbens of patients with early Parkinson's disease," NeuroImage, 49, pp. 2933-2939, 2010.

Julie Wang et al., "In vivo studies of the SERT-selective [18F]FPBM and VMAT2-selective [18F]AV-133 radiotracers in a rat model of Parkinson's disease," Nuclear Medicine and Biology, vol. 37, Issue 4, pp. 479-486, 2010.

Office Action issued in corresponding Russian Patent Application No. 2015155792/15 dated May 23, 2018.

Search Report issued in corresponding Russian Patent Application No. 2015155792/15 dated May 16, 2018.

Wu, H. et al., "SPECT Imaging of Dopamine Transporters With 99mTc-TRODAT-1 in Major Depression and Parkinson's Disease", J. Neuropsychiatry Clin. Neurosci., 2011, V.23, pp. 63-67, [on-line], retrieved from Internet on May 16, 2018: https://neuro.psychiatryonline.org/doi/pdf/10.1176/jnp.23.1.jnp63, the abstract; p. 64, col. 2, par.2; p. 65; table 2.

Wang, J.L. et al., "Comparison of the SERT-selective [18F]FPBM and VMAT2-selective [18F]AV-133 radiotracers in a rat model of Parkinson's Disease", Nucl. Med. Biol., 2010, V.37, pp. 479-486, [on-line], retrieved from Internet on May 16, 2018: https://www.ncbi.nlm.nih.gov/pmc/articles/PMC2909692/, the abstract.

Seibyl, J.P. et al., "Decreased Single-Photon Emission Computed Tomographic [123I]beta-CIT Striatal Uptake correlates with Symptom Severity in Parkinson's Disease", Annals of Neurology, 1995, V.38, pp. 589-598, [on-line], retrieved from Internet on May 16, 2018: https://www.ncbi.nlm.nih.gov/pubmed/7574455, the abstract; pp. 590-591.

Russian Office Action corresponding to Russian Application No. 2015155792104, dated Jul. 23, 2019.

Nu, Hao, et al., "SPECT Imaging of Dopamine Transporters With 99mTc-TRODAT-1 in Major Depression and Parkinson's Disease", J. Neuropsychiatry Clin. Neuosci., 2011, vol. 23, pp. 63-67, retrieved from website: [https://neuro.psychiatryonline.org/doi/pdf/10.1176/jnp.23.1.jnp63].

Tzen, Kai-Yuan, et al.,"Differential Diagnosis of Parkinson's Disease and Vascular Parkinsonism by 99mTc-TRODAT-1", The Journal of Nuclear Medicine, 2001, vol. 42, pp. 408-413, etrieved from website: [http://jnm.snmjournals.org/content/42/3/408.long].

Russia Rejection Decision corresponding to Russian Application No. 2015155792, dated Feb. 6, 2020 (with English translation).

Garmash A.V., et al., "Metrological Bases of Analytical Chemistry", URL: <http://biznes-ekspert.ru/_fr/2/garmasch.pdf>; 3rd Edition, Moscow, 2012, pp. 1-47 (with machine translation).

\* cited by examiner

Figure 1: SBR Ratio (Prior Art).
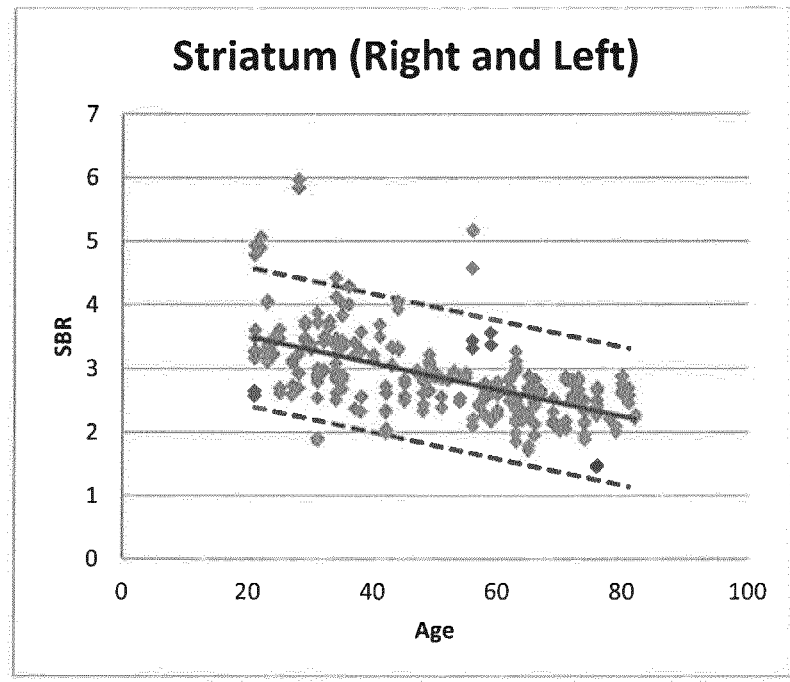
Figure 2: striatum R/L ratio
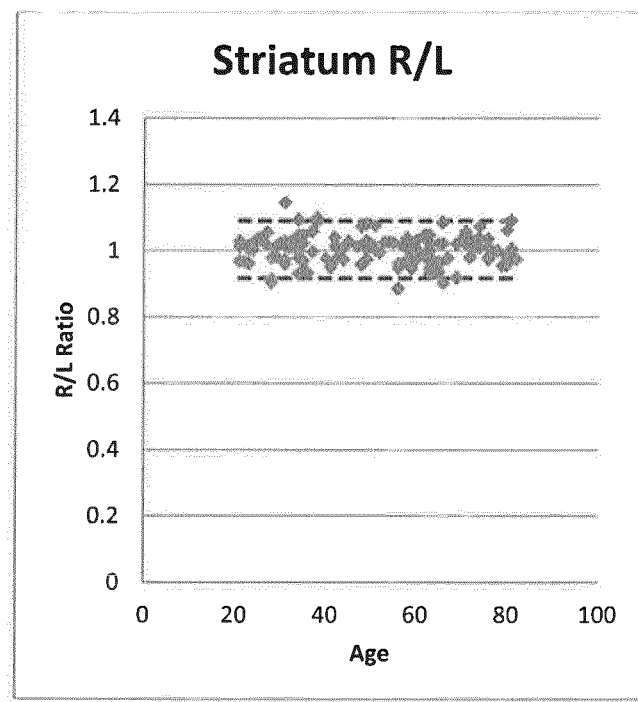

Figure 3: Left and Right Striatal Binding Values *vs* Age.
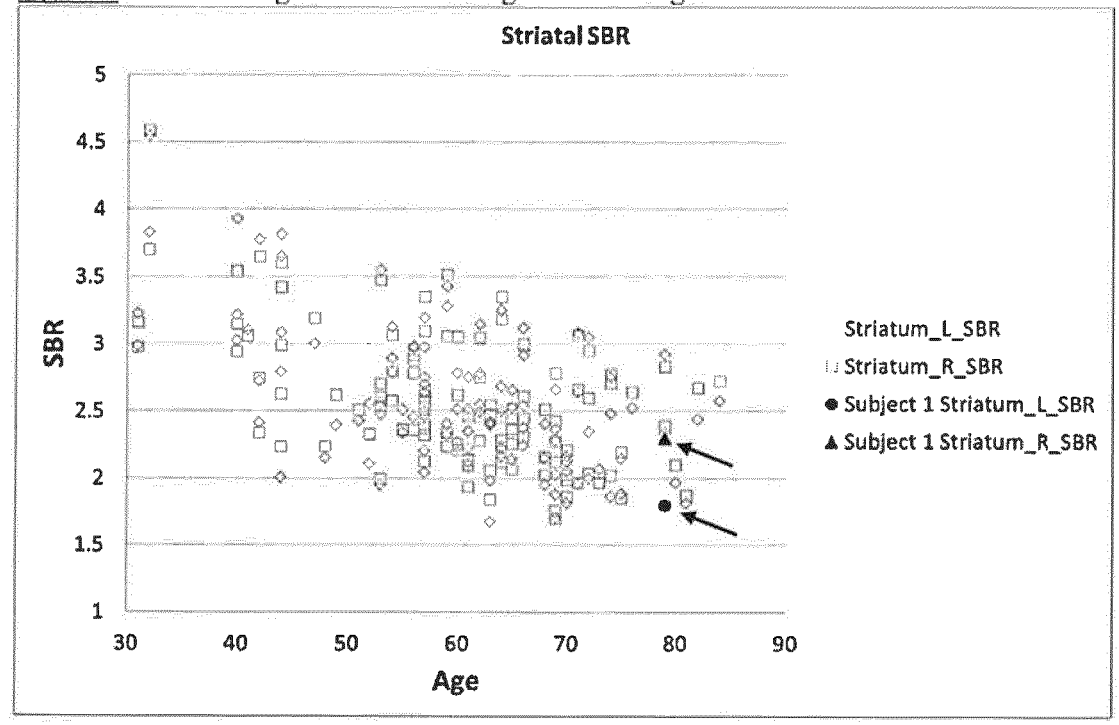
Figure 4: Asymmetry Index *vs* Age.
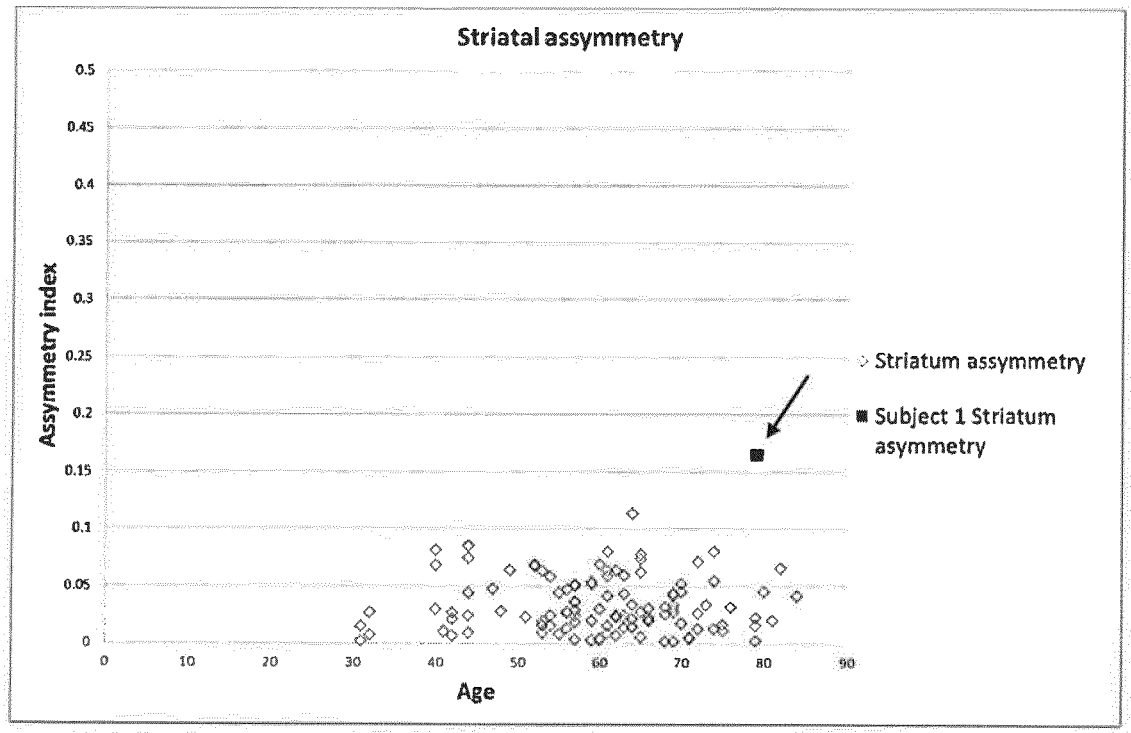

Figure 5: Putamen to Caudate Ratio *vs* Age.
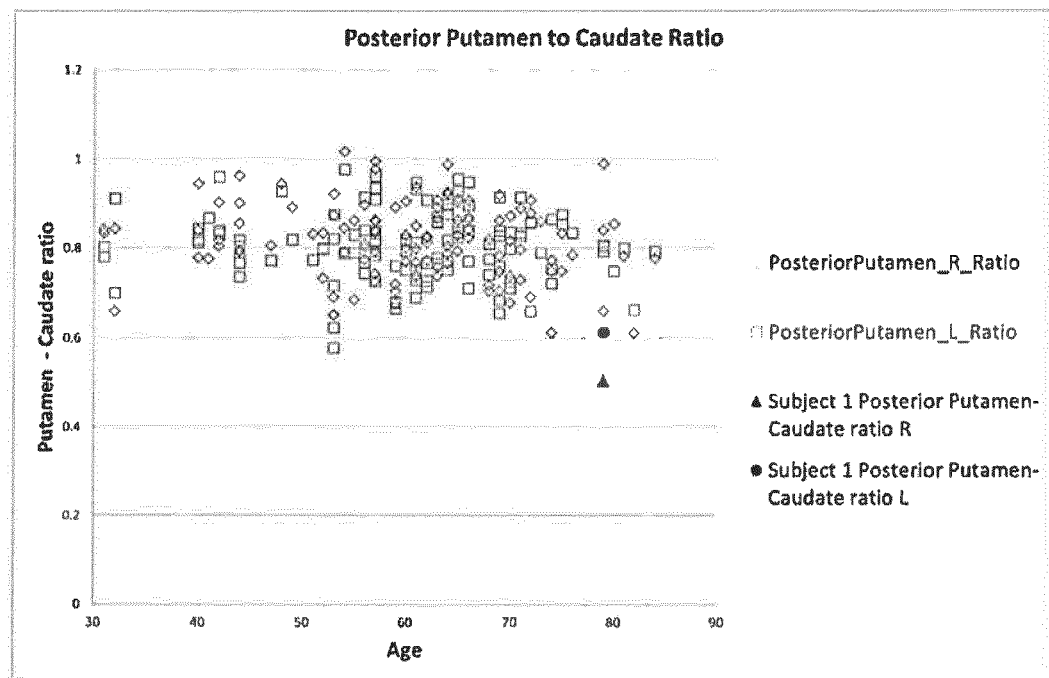

IMAGING NEUROLOGICAL DISEASE

FIELD OF THE INVENTION

Embodiments of the present invention relate to radiopharmaceutical imaging of the brain, in particular to dopamine transporter imaging of the striatum (or a portion thereof). A method of imaging to permit calculation of left:right striatum uptake ratios is provided, and the degree of asymmetry used to assist in the diagnosis of neurological diseases. Also provided are a method of diagnosis, method of patient selection, and method of therapy monitoring using the imaging method, and software tools for use in the method.

BACKGROUND TO THE INVENTION

Dopamine transporter imaging radiopharmaceuticals and brain imaging using such imaging agents have been described extensively in the art since the early 1990s. Laruelle et al [J. Cereb. Blood Flow Metab., 14, 982-984 (1994)] used the agent $^{123}$I-β-CIT and a ratio of striatal-to-background activity to give a figure proportional to dopamine transporter density.

Tatsch et al [Quart. J. Nucl. Med., 56(1), 27-38 (2012)] have reviewed approaches to the quantification of dopaminergic brain images. They note that ratios are normally calculated between the specific uptake of the radiopharmaceutical in the target region (e.g. stratum, caudate, putamen or subregions), and the uptake in a reference area (e.g. the cerebellum or other suitable region). The reference area represents non-specific binding of the radiopharmaceutical, and is this chosen for having either an absence or negligible number of specific tracer binding sites:

$$SBR = \frac{(\text{count density target } ROI - \text{count density reference } ROI)}{\text{count density reference } ROI}$$

where:
SBR=specific bind ratio or striatum binding ratio,
ROI=region of interest.

Neumeister et al [Psycholog. Med, 31(8) 1467-1473 (2001)] study the dopamine transporter using the radioiodinated tropane $^{123}$I-β-CIT in patients with seasonal affective disorder. Ratios between mean counts in the striatum and cerebellum were calculated. The cerebellum was used as the reference region because the dopamine transporter (DaT) density there was known to be low, and hence the cerebellum was assumed to represent non-specific bound radioactivity as well as free radioactivity.

Lauer et al [J. Neural Transm., 108(6), 661-670 (2001)] studied human schizophrenia human patients and controls with PET imaging using the glucose metabolism radiotracer [$^{18}$F]-FDG, and the dopamine storage radiotracer [$^{18}$F]-FDOPA. Since the radioactive doses used were different for the patients and controls, left/right ratios of the hemispheres and frontal cortices were calculated for the [$^{18}$F]-FDG scans to permit comparison of patients with control data from the literature. A higher degree of [$^{18}$F]-FDOPA asymmetry was reported for one patient compared to another two, but no comparison with normal subjects was reported for [$^{18}$F]-FDOPA.

Nakagawa et al [Ann. Nucl. Med., 19(4), 267-275 (2005)] studied parkinsonism patients with $^{18}$F-FDG and the striatal $D_2$ receptor tracer $^{11}$C-raclopride. In order to obtain specific $D_2$ receptor binding, they subtracted cerebellar activity from the striatal radioactivity counts. L/R asymmetry of [$^{18}$F]-FDG was compared with L/R asymmetry of $^{11}$C-raclopride in patients. No comparison for either tracer in normal subjects was performed.

Cai et al [Neural Regen. Res., 5(2), 92-97 (2010)] studied the effect of levodopa on dopaminergic neurons in animals using the dopamine transporter imaging radiopharmaceutical $^{99m}$Tc-TRODAT-1. They calculated a left/right ratio of specific uptake ratio after surgical intervention based on animal sacrifice and counting of tissue samples. The animal control group had been subjected to sham surgery and were not a true normal dataset.

Gleave et al [Nucl. Med. Biol., 38(5), 741-749 (2011)] studied the dopamine transporter imaging radiopharmaceutical $^{123}$I-altropane in an animal model of Parkinson's disease. Gleave et al calculated an "altropane ratio" of the left to right side based on animal sacrifice, and tissue sample counting with subtraction of cerebellum uptake from the striatal counts, to give specific uptake, before calculation of the left/right ratio. The left/right ratios were compared with animal behaviours, but no comparison with a normal control was performed.

For dopamine transporter imaging with $^{123}$I-ioflupane, Soderlund et al [J. Nucl. Med., 54(5), 714-722 (2013)] advocate a combined approach based on: (i) visual assessment of patient scans, (ii) semi-quantitative assessment based on SBR (based on striatum uptake with occipital cortex uptake as the reference region), and CPR (caudate-to-putamen ratio). They suggest that this reduces intra-observer variability.

Correction factors may be needed to permit comparison of SBR and similar ratios obtained using different camera systems within a single imaging facility and between different sites. Associated software tools have been studied extensively. These are discussed by Zaknun et al [Quart, J. Nucl. Med. Mol. Imaging, 51, 194-203 (2007)] and Tatsch et al (vide supra).

Katzenschlager et al [Ann. Neurol., 53(4), 489-496 (2003)], Zijlmans et al [Movement Dis., 22(9), 1278-1285 (2007)] and Contrafatto et al [Clin. Neuropharmacol., 34(2), 71-73 (2011)] have proposed a 'striatal asymmetry index' (SAI) to establish the degree of asymmetry of DaTSCAN™ uptake, where:

$$SAI = \frac{(Y-Z)}{(Y+Z)} \times 2 \times 100$$

where Y & Z are the striatal binding indexes (SBIs) for the 2 different sides.

The SBI is calculated from the ipsilateral (same side) caudate and putamen ROI radioactivity counts, using the algorithm:

$$SBI = \frac{(ROI \text{ caudate} + ROI \text{ putamen}) - O}{O}$$

where O=mean counts per pixel in the occipital cortex (background).

The striatal asymmetry index (SAI) is thus still based on the background subtraction approach of the SBR (see above). The papers mention SAI ranges for normals, but there is no systematic discussion of the width of that range or how it may be affected by e.g. age. SAI ranges between different cohorts of patients are compared, but the discussion does not address left/right symmetry (or lack of symmetry) and the comparison with normal subjects. The SAI is largely used to look at subjects with symptoms in their left or right side, and the authors attempt to find associations between the SAI and these symptoms.

It is conventional in the art to compare the patient image with age-matched controls, since it is known that the striatal uptake of a dopamine transporter radiopharmaceutical declines with age. Such comparison requires the use of normal image databases. Such databases are, however, only really meaningful for a coherent set of data, which may well mean the same camera, same software, same imaging protocol etc.

There is therefore still a need for dopamine transporter imaging methodology which is robust enough to give comparable results across a range of camera types, and avoids the large spread of data seen in multi-site studies, which is statistically sound, and is suitable for any age of patient.

In dopamine transporter radiopharmaceutical imaging, when uptake of the radiopharmaceutical in the brain is quantified, the values obtained vary significantly depending on the camera configuration and set-up, image acquisition parameters, and many other factors. It has therefore so far proved impossible to establish a meaningful normal database that is built on data from more than one camera type, without considerable effort to apply 'correction factors'.

In the current GE Healthcare product 'DaTQUANT™, normal data from non-GE cameras is removed from the data set before calculating. In the Hermes BRASS product, correction factors are applied but this significantly compromises the utility and applicability of the 'normal' average values reported.

An embodiment of the present invention is based on the observation that left:right symmetry of striatum uptake in the normal patient population is maintained independent of the age and gender of the patient. This symmetrical left/right striatum uptake is shown to be independent of camera type and image acquisition parameters, and is proposed as a more robust way to generate both a normal database and patient comparator data—wherein imaging data can be compared without the need for complex correction factors.

Visual assessment of dopamine transporter radiopharmaceutical images is generally used to determine whether brain uptake patterns are normal or abnormal. Quantification of DaTSCAN™ uptake in the striatum (putamen and caudate separately and in sum) and comparison with average values obtained from a normal population has been proposed as a more sensitive and more reproducible method of detecting abnormal (reduced) uptake suggestive of Parkinson's disease (PD) and Parkinsonian Syndromes.

A problem with this method is that average striatum binding ratio (SBR) and related values vary significantly between camera types, and even between the same camera type at different clinical sites—even when the same radiopharmaceutical is used. The reason for such a wide variation is not yet fully understood, but factors such as collimator type and image reconstruction methodology have been suggested. The consequence is that the 'average' value of SBR cannot easily be transferred from one site to another as a comparator for the subject. A normal database that is constructed with data from more than one site shows a very wide spread of values for average SBR and associated regions of interest, such as entire striatum, putamen or caudate.

Furthermore the standard deviation of 'normal' SBR even from a single site and camera is large—due to the natural variation within the normal human population. If the data set includes data from multiple cameras/sites, then the statistical variation becomes wider still. The effect is that a subject with e.g. early PD and a relatively low level of reduced striatal uptake may lie within the apparently 'normal' population of such a data set (i.e. within 1 to 2 standard deviations of the mean value), when a more statistically robust, coherent normal data set would have flagged the deviation from normal uptake.

An embodiment of present invention is based on an analysis of left-right symmetry of striatal uptake. Surprisingly, the left-right symmetry of such uptake has been found to be maintained in healthy subjects irrespective of subject age and gender. Thus, for a normal population, the ratio left striatum:right striatum (absolute or SBR) is close to 1.0 with low standard deviation. This has been found to hold true even when patient image data from different clinical sites and/or different camera systems are used. Furthermore, it is not necessary to apply any correction factors for different cameras employed in multi-centre datasets, as the symmetry is 'self-calibrating' for each image.

In neurological disorders where there is loss of dopaminergic function, one side is usually more affected than the other and the left:right ratio drifts away from 1.0. Comparison of the left:right ratio with that of the normal population therefore gives a way to assess whether a subject has abnormal uptake compared to a normal population that is independent of camera set up and site. This is expected to be especially valuable in earlier stages of such disease, when a deviation in the left:ratio for the patient compared to the normal population may be detected while the SBR and similar ratios remain within the normal range (due to the much larger standard deviation of SBR as described above). This is expected to improve accuracy and sensitivity and also to facilitate earlier diagnosis of disease. It will also permit earlier differentiation of PD/PS and Lewy Body Dementia diseases from other disorders with similar clinical symptoms e.g. ET, AD, vascular and drug-induced PS.

A further benefit is that when comparing left:right uptake values, absolute values can be used rather than comparing target:background ratios. That eliminates the need for more complex calculations, and reduces statistical variation due to subtraction of two numbers, each having an associated error bar. This is particularly important with respect to the counts in the background/reference region. Those counts will be intrinsically low—hence the error bar or "noise" is relatively large. Furthermore, the conventional SBR calculates two ratios, so the error bar is compounded by the calculation. Subtraction of such a figure therefore introduces a statistical variation. Differences introduced through variations in background in left and right hemispheres are thereby avoided, and an even narrower distribution of the normal data can be expected.

Furthermore, the method of the present invention does not require analysis to carry out comparison with age-matched and gender-matched patients/controls. That is because the striatum L/R ratio is close to 1.0 in normal subjects regardless of age and gender. This is a useful simplification. Furthermore, whereas the diagnostic 'dynamic range' of SBR is decreased in patients of advanced age due to the natural reduction of striatal uptake even in normal subjects, this limitation is not present when comparing left:right uptake.

BRIEF DESCRIPTION OF THE DRAWINGS

In FIGS. 1 and 2, the solid line shows the mean, and the dotted line the 95% confidence limit.

FIG. 1 shows the prior art SBR determination for normal human subject imaging data. This shows a considerable spread of values, and a variation with the age of the subject.

FIG. 2 shows the striatum L/R ratio calculation for the same data set as FIG. 1.

FIG. 3 shows the left and right striatal binding values from the normal data set of Example 3. The data from Subject 1 of Example 4, a male 79 years old Parkinson's patient based on clinical diagnosis, (solid circle and triangle, respectively, also marked by the arrows) are included for comparison. Subject 1 is an illustrative example. It can be seen that, based on SBR alone, Subject 1's ratios are within the normal ranges as indicated by the hollow diamonds and squares.

FIG. 4 shows the asymmetry index (or normalised left-right asymmetry) of the normal data set of Example 3. Subject 1 is illustrative data from Example 5. The data for Subject 1 (see FIG. 3; solid square, pointed out by arrow) is clearly outside the range given by the normal values (hollow diamonds), hence indicating abnormality of Subject 1's DaTSCAN image that would not be obvious when merely studying striatal binding ratio alone as per FIG. 3.

FIG. 5 shows the ratio of uptake in the posterior putamen to the caudate for the normal group, with data for Subject 1 superimposed. The normal range is defined by the hollow diamonds (left striatum) and hollow squares (right striatum). As seen, especially the right-hand ratio of Subject 1's posterior putamen to caudate ratio (solid triangle, pointed out by arrow) was below the normal range which again suggests abnormality that is not visible when merely studying striatal binding as in FIG. 3.

DETAILED DESCRIPTION OF THE INVENTION

In a first aspect, the present invention provides a method of imaging useful in the diagnosis of neurological disease, which comprises: provision of a subject previously administered with a radiopharmaceutical suitable for imaging dopamine function; assessing the uptake of the radiopharmaceutical in an equivalent region of: the left; and the right; of the striatum of the brain of the subject; calculating the ratio of the uptake in the equivalent left and right striatum region from step (ii); comparing the ratio for the subject from step (iii) with a normal range of such ratios for normal subjects.

By the term "method of imaging" is meant a method which generates images of the subject—typically two-dimensional or three-dimensional, in colour or black and white, more particularly colour. The images may be of the whole subject or a part thereof, i.e. a region of interest (ROI). For the present invention, the ROI is suitably the brain of the subject or a region within the brain.

By the term "neurological disease" is meant a disorder with pathological features affecting brain function such as dementia, movement disorders or drug-induced disorders of the human or mammalian body. These include, but are not limited to: Parkinson's disease; Parkinson's syndromes (progressive supranuclear palsy, multiple system atrophy, corticobasal degeneration); Lewy body dementia (DLB); Alzheimer's disease and AD-HD. The unequivocal diagnosis of these during life can be difficult, due to overlapping symptoms of other diseases such as Essential Tremor, Alzheimer's disease and drug induced or vascular Parkinsonism. Hence, understanding whether the symmetry of equivalent left and right regions of the brain has been maintained is still useful. This is described more fully in the second aspect (below).

By the term "subject" is meant a mammal in vivo, particularly the intact mammalian body in vivo, and more particularly a living human subject. The term "normal range" is as defined in the second aspect (below).

The term "radiopharmaceutical" has its' conventional meaning, and refers to an imaging agent wherein the imaging moiety is a radioisotope. The radiopharmaceutical is labelled with a radioisotope suitable for medical imaging in vivo. By the term "imaging agent" is meant a compound suitable for imaging the mammalian body. Such imaging agents are designed to have minimal pharmacological effect on the mammalian subject to be imaged. In an embodiment the imaging agent can be administered to the mammalian body in a minimally invasive manner, i.e. without a substantial health risk to the mammalian subject when carried out under professional medical expertise. Such minimally invasive administration is more particularly intravenous administration into a peripheral vein of the subject, without the need for local or general anaesthetic.

By the term "dopamine function" is meant imaging dopaminergic neurons of the midbrain, in particular: dopamine synthesis; dopamine storage and dopamine reuptake. These are assessed by the following types of radiopharmaceutical respectively: a DOPA decarboxylase activity radiopharmaceutical; a VMAT2 binding radiopharmaceutical; a dopamine transporter binding radiopharmaceutical.

For further details see Nikolaus et al, [Rev. Neurosci., 18, 439-472 (2007)] and Hefti et al [PET Clin., 5, 75-82 (2010)]. In an embodiment, the dopamine function may be presynaptic dopamine function.

The term "DOPA decarboxylase activity radiopharmaceutical" refers to radiotracers which show the metabolism of the drug DOPA (L-3,4-dihydroxyphenylalanine). Such tracers may be DOPA itself labelled with $^{18}F$ ($^{18}F$-DOPA also known as $^{18}F$-FDOPA), or $^{11}C$ ($^{11}C$-DOPA), or analogues thereof. These are described by Elsinga et al [Curr. Med. Chem., 13, 2139-2153 (2006)]. The synthesis of $^{18}F$-FDOPA is described by Kao et al [Ann. Nucl. Med., 25(5), 309-316 (2011)].

The abbreviation "VMAT2" refers to the vesicular monoamine transporter type 2. The term "VMAT2 binding radiopharmaceutical" refers to a radiopharmaceutical suitable for imaging VMAT2. Suitable such radiopharmaceuticals include dihydrotetrabenazine compounds labelled with $^{11}C$ or $^{18}F$, such as [$^{11}C$]-dihydrotetrabenazine ([$^{11}C$]DTBZ) [Hefti et al, PET Clin., 5(1), 75-82 (2010)]. An automated synthesis of $^{11}C$-DTBZ is described by Zhang et al [Molecules, 17(6), 6697-6704 (2012)]. $^{18}F$-fluoroalkyl dihydrotetrabenazine derivatives are described by Kilbourn et al [Nucl. Med. Biol., 34(3), 233-237 (2007)], Goswami et al [Nucl. Med. Biol., 33(6), 685-694 (2006)] and Jahan et al [EJNMMI Res., 1(1), 1-13 (2013)]. A more particular such radiopharmaceutical is the PET radiotracer [$^{18}F$]AV-133 [(+)-2-Hydroxy-3-isobutyl-9-(3-fluoropropoxy)-10-methoxy-1,2,3,4,6,7-hexahydro-11bH-benzo[a]quinolizine:

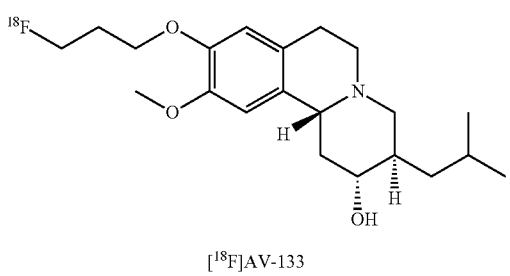 [SMILES: COc1cc2c(cc1OCCC[18F])CCN1C[C@@H](CC(C)C)[C@H](O)C[C@H]21]

[18F]AV-133

[18F]AV-133 is described by Hefti et al [PET Clin., 5(1), 75-82 (2010)]. Zhu et al describe an improved synthesis of [18F]AV-133 [Nucl. Med. Biol., 37(2), 133-141 (2010)].

The term "dopamine transporter radiopharmaceutical" has its' conventional meaning in the field of radiopharmaceutical imaging. It refers to an imaging agent for the pre-synaptic dopamine transporter system in vivo, also known as the dopamine reuptake system. The dopamine transporter system is described by Elsinga et al [Curr. Med. Chem., 13, 2139-2153 (2006)], as well as in *Dopamine Transporters: Chemistry, Biology, and Pharmacology* [Trudell et al (Eds), Wiley-Blackwell (2008)]. Dopamine transporter radiopharmaceuticals have been reviewed by Shen et al [J. Biomed. Biotechnol., Article 259349 (2012)], and Wang et al J. Biomed. Biotechnol., Article 412486 (2012)].

The phrase "assessing the uptake" refers to techniques for detecting the radioactive emissions from the radiopharmaceutical within the subject. This is suitably carried out using a gamma camera or positron emission camera as is known in the art. In the present method, the uptake measured is more particularly the absolute uptake—without background correction or background subtraction being carried out. The uptake is also measured for the left and right 'equivalent region' concurrently, and for a defined period of time—i.e. the same acquisition start time and finish time.

By the phrase "without background correction" is meant that the absolute uptake in the 'equivalent region' is used directly in the ratio calculation. Thus, no subtraction to remove counts from a reference region of the patient's brain or other tissues (e.g. to seek to remove or compensate for non-specific uptake), is carried out. This is a significant difference over the prior art, where such subtraction is the conventional wisdom.

The term "striatum" has its conventional meaning, and refers to a subcortical part of the brain. The striatum is divided into two sectors: the caudate nucleus and putamen, which are divided by a white matter tract called the internal capsule.

The terms "left" and "right" follow conventional clinical practice and refer to the patient's left side, and the patient's right side respectively. In medical tomographic imaging, it is conventional to view two-dimensional images which display horizontal 'slices' of the uptake of the radiopharmaceutical at various positions within the patient's brain. In the images of the brain, these tomographic slices each have a left and a right side corresponding to the subject's left and right side and left and right hemisphere of the brain. Brain tomographic imaging is described in *Functional Cerebral SPECT and PET Imaging* [Van Heertum et al (eds), 4th Edition, Lippincott Williams and Wilkins (2009)] and *Neuroimaging in Dementia* [Barkhof et al, Springer (2011)].

By the term "equivalent region" is meant a region of the same volume (for 3-dimensional imaging) or the same area (for 2-dimensional imaging), on the left and right side of the brain. This could be as an area of interest (AOI), volume of interest (VOI) or region of interest (ROI). Software tools are known in the art to assist in such methodology. Such software tools are commercially available—typically from the commercial supplier of the gamma camera or positron camera. Other such software tools are described by Tatsch et al [Quart. J. Nucl. Med., 56(1), 27-38 (2012)].

The size of the 'equivalent region' is up to the size of the whole striatum or a portion thereof. The person skilled in the art will know that the minimum such 'equivalent region' chosen will be dictated by good counting statistics—i.e. where the radioactive counts detected are well above general background. This is governed by variables such as: the amount of radioactivity administered; the emission characteristics of the radioisotope; the sensitivity of the camera; the acquisition time, the radius of rotation of the detectors on certain cameras etc. Consequently, direct comparison of the two uptake figures (left and right), is representative of the relative uptake in the left and right striatum. It does not matter whether one calculates AB (i.e. left/right) or B/A (i.e. right/left) ratio—as long as a consistent approach is taken. The ratio calculated in the present method thus provides a measure of left/right asymmetry in the subject image.

The terms "comprising" or "comprises" have their conventional meaning throughout this application and imply that the agent, composition or method must have the essential features, components or steps listed, but that others may be present in addition. The term 'comprising' includes as a possible subset "consisting essentially of" which means that other features or components are excluded, i.e. only those listed are present.

The method of the first aspect may be carried out on the same subject on one or more occasions, i.e. at different time intervals. Multiple such determinations on the same subject permit the longitudinal monitoring of a neurological disease, i.e. of disease progression. This can be carried out with or without therapy. The former is described as the fourth aspect (below).

In an method of the first aspect, the radioisotope of the radiopharmaceutical is more particularly suitable for either PET or SPECT imaging in vivo. PET imaging radiopharmaceuticals are often also termed 'radiotracers'. The radioisotope can be metallic (i.e. a radiometal), or a non-metal. When the imaging moiety is a radiometal, suitable radiometals can be either positron emitters such as $^{64}$Cu, $^{48}$V, $^{52}$Fe, $^{55}$Co, $^{94m}$Tc or $^{68}$Ga; γ-emitters such as $^{99m}$Tc, $^{111}$In, $^{113m}$In, or $^{67}$Ga. In an embodiment, radiometals may be $^{99m}$Tc, $^{64}$Cu, $^{68}$Ga and $^{111}$In. More particularly, radiometals are γ-emitters, especially $^{99m}$Tc.

When the imaging moiety is a non-metal, it can be a gamma-emitter or a positron emitter. Gamma-emitting radiohalogens are suitably chosen from $^{123}$I, $^{131}$I or $^{77}$Br. A gamma-emitting radioactive halogen may be $^{123}$I. When the imaging moiety is a positron-emitting radioactive non-metal, suitable such positron emitters include: $^{11}$C, $^{13}$N, $^{15}$O, $^{17}$F, $^{18}$F, $^{75}$Br, $^{76}$Br or $^{124}$I. In an embodiment, positron-emitting radioactive non-metals may be $^{11}$C, $^{13}$N, $^{18}$F and $^{124}$I, particularly $^{11}$C and $^{18}$F, more particularly $^{18}$F.

In the method of the first aspect, the radiopharmaceutical suitable for imaging dopamine function may be a VMAT2 imaging radiopharmaceutical, or a dopamine transporter imaging radiopharmaceutical, more particularly a dopamine transporter imaging radiopharmaceutical. The dopamine transporter radiopharmaceutical comprises a radiolabelled tropane, and more particularly comprises a 3-phenyltropane. The term "tropane" has its conventional meaning in the art.

PET tropanes have been reviewed by Riss et al [J. Lab. Comp. Radiopharm., 56(3-4), 149-158 (2013)], and Elsinga et al [Curr. Med. Chem., 13, 2139-2153 (2006)]. SPECT tropanes have been reviewed by Wang et al [J. Biomed. Biotechnol., Article 412486 (2012)].

The dopamine transporter radiopharmaceutical may comprise a adioisotope chosen from $^{123}$I or $^{99m}$Tc for SPECT, or $^{18}$F or $^{11}$C for PET, more particularly $^{123}$I or $^{18}$F. The dopamine transporter radiopharmaceutical may comprise $^{123}$I-ioflupane (DaTSCAN™), $^{18}$F-ioflupane, $^{123}$I-Altropane, $^{123}$I-PE2I, $^{11}$C-PE2I, $^{123}$I-IPT, $^{123}$I-β-CIT, $^{18}$F-β-CFT, $^{99m}$Tc-TRODAT or $^{99m}$Tc-technepine. IN an embodiment, the dopamine transporter radiopharmaceutical comprises $^{123}$I-ioflupane (DaTSCAN™), $^{18}$F-ioflupane or $^{123}$I-Altropane, more particularly $^{123}$I-ioflupane (DaTSCAN™) or $^{123}$I-Altropane, with $^{123}$I-ioflupane (DaTSCAN™) being the ideal.

The structures of these agents are given by Shen et al (J. Biomed. Biotechnol., Article 259349 (2012)], and are shown in Scheme 1 below:

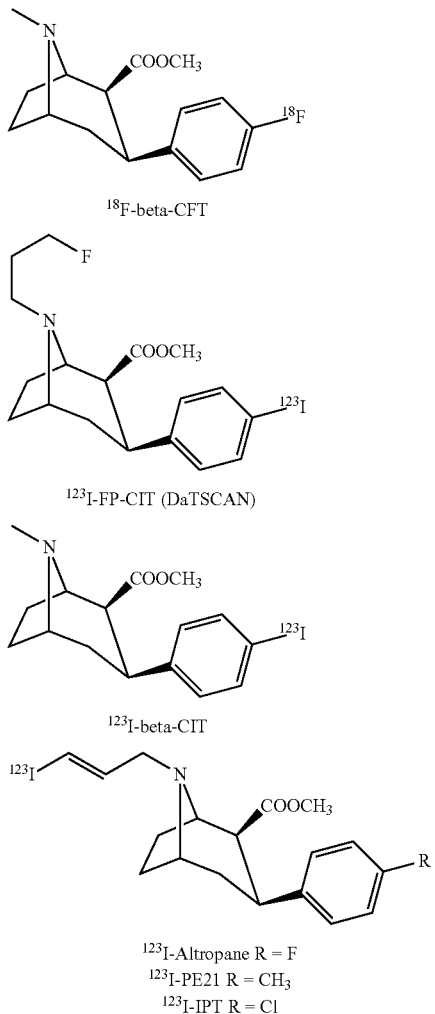

Scheme 1: tropane-based DaT agents.

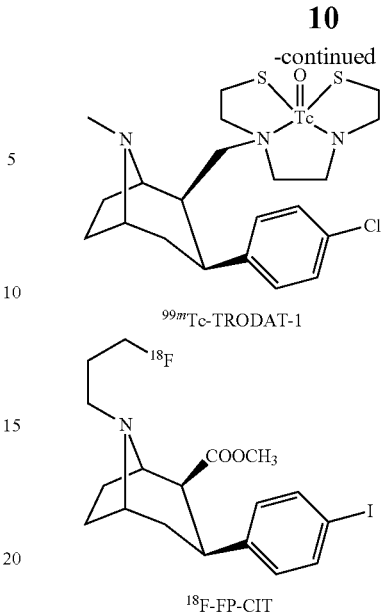

In step (ii) of the method of the first aspect, "assessing the uptake" is particularly based on the absolute uptake as described above. The method of the first aspect may exclude further analysis to carry out comparison with age-matched and gender-matched patients/controls, or to correct for camera type.

In a tomographic image, the striatum appears comma-shaped—with the caudate as the dot/ball-shaped part of the comma, and the putamen as the tail of the comma. In the method of the first aspect, the equivalent region of step (ii) may be chosen from: the whole striatum; the caudate; the putamen; or combinations thereof.

In an embodiment, the equivalent region of step (ii) is the putamen, and more particularly the posterior putamen. That is because the caudate exhibits the highest uptake, even in Parkinson's syndrome patients—whereas putamen uptake tends to decline with the progression of Parkinson's diseases. Thus, the putamen is most likely to be the first to show asymmetric uptake, in particular the posterior putamen. Hence, using a left/right ratio based on putamen uptake is the most sensitive indicator of PD, and may permit early diagnosis—before perhaps clinical symptoms become evident.

In some embodiments the equivalent region of step (ii) is the combination of all the following: the whole striatum; the caudate; the putamen; the posterior putamen such that ratios for each of these regions are determined. That is expected to give more useful diagnostic information.

In the method of the first aspect, the assessing of step (ii) and/or the calculating of step (iii) may be carried out via tomographic imaging, more particularly positron emission tomography (PET) or single photon emission tomography (SPECT).

The method of the first aspect may further comprise one or more of the following: (I) calculating a caudate:putamen or putamen:caudate ratio for the left and right striatum separately; (II) calculating a striatal binding ratio (SBR; as defined above) for left and right hemisphere; (III) calculating the ratio of counts in equivalent left and right regions of the brain; (IV) comparing left:right (or right:left) ratios obtained in (III) with normal values.

This additional data complements the striatum binding ratio, and is particularly useful in the further clinical diagnosis of patients where the ratio may appear 'normal', but the asymmetry compared to the normal population, clinical symptoms or other criteria suggest a neurological disease. See the discussion in the second aspect (below).

The dopamine transporter radiopharmaceuticals of the first aspect can be obtained as follows. DatScan™ ($^{123}$I-ioflupane) is commercially available in Europe and the USA from GE Healthcare. Other agents can be prepared via the methods cited above, as well as the references cited by Shen et al [J. Biomed. Biotechnol., Article 259349 (2012)], and Nikolaus et al, [Rev. Neurosci., 18, 439-472 (2007)].

In a second aspect, the present invention provides a method of diagnosis which comprises the method of imaging of the first aspect, where the comparing of step (iv) is with a database of such ratios, wherein the database contains such ratios for normal subjects; and which further comprises: (v) when the ratio from step (iv) is within the normal range, the subject is classified as having a normal presentation; (vi) when the ratio from step (iv) is outside the normal range, the patient is classified as suffering from a neurological disease.

Embodiments of the method of imaging and the radiopharmaceutical suitable for imaging presynaptic dopamine function in the method of diagnosis of the second aspect, are as described in the first aspect (above).

The database of step (iv) of the second aspect suitably comprises the ratio of step (iii) for a group of normal subjects, and may further comprise such ratios for patients having a known, defined neurological condition. An important benefit of embodiments of the present invention is that such ratios can readily be compiled from a range of clinical datasets, even if collected on different cameras, without the need for correction factors. This facilitates the compilation of a larger, usable dataset—which in turn means the data within the database carries a more powerful statistical significance. The database comparison is suitably carried out using the software tool of the fifth aspect.

The term "normal range" refers to the uptake ratio of the first aspect for the normal subjects within the database. The ordinary person skilled in art can choose a suitable confidence limit, but a 95% confidence limit corresponding to approximately ±2 standard deviations of the mean from the normal range, is often selected.

By the term "normal presentation" is meant that the left/right ratio determined for the subject under diagnosis is within the normal range. This indicates that, either the subject is normal, or that the patient is suffering from a neurological condition which exhibits a symmetric pattern. Thus, certain neurological conditions exhibit a 'normal' striatum left/right ratio, i.e. close to 1.0.

In the method of the second aspect, neurological diseases where the left/right ratio of step (iii) is expected to fall outside the normal range (i.e. show left/right asymmetry) are: Parkinson's disease or Parkinson's syndromes such as Multiple System Atrophy (MSA) and Progressive Supranuclear Palsy (PSP).

In the method of the second aspect, examples of neurological diseases where the left/right ratio of step (iii) is expected to fall within the normal range (i.e. show left/right symmetry) are: drug-induced parkinsonism, vascular pseudo-parkinsonism, Alzheimer's disease, essential tremor (ET) and DLB.

The finding of a "normal presentation" can be used to exclude certain neurological conditions which do exhibit an asymmetric ratio, and thus differentiate PD, MSA and PS for such subjects. In combination with the subject's other clinical symptoms, and/or further medical imaging or testing, this information may still be valuable in patient diagnosis and management. Thus, e.g. Contrafatto et al have shown that the SAI (as defined above) can be used to differentiate Parkinson's disease from vascular parkinsonism [Acta Neurol. Scand., 126(1), 12-16 (2012)]. Furthermore, for DLB, the striatum left/right ratio is expected to show a 'normal presentation' but further analysis, in particular determination of the SBR is expected to be valuable—since the SBR is expected to be low for such subjects. The finding of a 'normal presentation' can then be put into context using other tests, such as additional steps (I)-(IV) of the first aspect—to seek to finalise the diagnosis.

In a third aspect, the present invention provides a method of selecting or excluding a subject for a particular therapy of a neurological disease, which comprises the method of imaging of the first aspect, or the method of diagnosis of the second aspect.

Embodiments of the method of imaging and the radiopharmaceutical suitable for imaging presynaptic dopamine function in the method of selection of the third aspect, are as described in the first aspect (above). Embodiments of the method of diagnosis in the third aspect, are as described in the second aspect (above). Embodiments of the neurological disease in the third aspect are those diseases described in the second aspect as showing left/right asymmetry, i.e. Parkinson's disease or Parkinson's syndromes.

When the method of imaging of the first aspect, or the method of diagnosis of the second aspect permits a positive diagnosis of a given neurological disease, then the appropriate therapy for the disease is selected for the subject.

The third aspect also includes excluding from anti-Parkinsonian therapy a subject shown to have an apparently normal L/R striatal ratio using the methods of the first or second aspect. This exclusion is important, since it helps avoid misdiagnosis and unsuitable therapies which cannot benefit the subject, and only risk causing harm.

The third aspect also includes deselecting from therapy a subject already undergoing therapy for a neurological condition, whose existing course of treatment/therapy, is found to be unsuitable after the imaging of the first aspect, or the diagnosis of the second aspect establishes that the treatment/therapy is misdirected due to a previous misdiagnosis. This is particularly important if e.g. the subject has been misdiagnosed with PD, and is receiving anti-Parkinson's medication or therapy—but is found by the method(s) of the invention to be suffering from a different condition.

In a fourth aspect, the present invention provides a method of monitoring the efficacy of a course of therapy of a neurological disease of a subject, which comprises the method of imaging of the first aspect, or the method of diagnosis of the second aspect.

Embodiments of the method of imaging and the radiopharmaceutical suitable for imaging presynaptic dopamine function in the method of monitoring of the fourth aspect, are as described in the first aspect (above). Embodiments of the method of diagnosis in the fourth aspect, are as described in the second aspect (above). Embodiments of the neurological disease in the fourth aspect are those diseases described in the second aspect as showing left/right asymmetry, i.e. Parkinson's disease or Parkinson's syndromes.

In a fifth aspect, the present invention provides a software tool suitable for carrying out: step (ii) and/or step (iii) of the method of imaging of the first aspect; or one or more of steps (ii) to (v) of the method of diagnosis of the second aspect; or the method of selection of the third aspect; or the method of monitoring of the fourth aspect; or combinations of one or more of (a) to (d).

Embodiments of the method of imaging and the radiopharmaceutical suitable for imaging presynaptic dopamine function in the fifth aspect, are as described in the first aspect (above). Embodiments of the method of diagnosis in the fifth aspect, are as described in the second aspect (above).

The software tool of the fifth aspect more particularly runs on a personal computer, a gamma camera or a PET camera workstation. The software tool of the fifth aspect may comprise the database of L/R ratios described in the second aspect.

In a sixth aspect, embodiments of the present invention provide the use of the radiopharmaceutical suitable for imaging presynaptic dopamine function of the first aspect, in one or more of: the method of imaging of the first aspect; the method of diagnosis of the second aspect; the method of selection of the third aspect; or the method of monitoring of the fifth aspect.

Embodiments of the method of imaging and the radiopharmaceutical suitable for imaging presynaptic dopamine function in the sixth aspect, are as described in the first aspect (above). Embodiments of the method of diagnosis in the sixth aspect, are as described in the second aspect (above).

In a seventh aspect, the present invention provides the use of the software tool as defined in the fifth aspect in one or more of: the method of imaging of the first aspect; the method of diagnosis of the second aspect; the method of selection of the third aspect; or the method of monitoring of the fifth aspect.

Embodiments of the method of imaging and the radiopharmaceutical suitable for imaging presynaptic dopamine function in the seventh aspect, are as described in the first aspect (above). Embodiments of the method of diagnosis in the seventh aspect, are as described in the second aspect (above).

In an eighth aspect, the present invention provides the use of a tomographic imaging device in one or more of: the method of imaging of the first aspect; the method of diagnosis of the second aspect; the method of selection of the third aspect; or the method of monitoring of the fourth aspect.

Embodiments of the method of imaging and the radiopharmaceutical suitable for imaging presynaptic dopamine function in the eighth aspect, are as described in the first aspect (above). Embodiments of the method of diagnosis in the eighth aspect, are as described in the second aspect (above).

In a ninth aspect, the present invention provides a database as described in the second aspect.

EXAMPLES

Embodiments of the present invention is illustrated by the non-limiting Examples detailed below. Examples 1 and 2 are theoretical Examples, whereas Examples 2-5 are based on clinical data.

Example 1 is a comparative Example which shows the calculation of SBR using data from: (i) a range of camera manufacturers (Group A); (ii) a single manufacturer (GE; Group B) and (iii) a patient. The variation in Group A is so wide that there is almost no value in it for comparison with patient data. Even with Group B, the normal range is too wide to be useful for comparative purposes. This demonstrates the difficulties with the current methodology.

Example 2 applies the method of the present invention. In the normal population, for each individual subject the values for left and right are likely very close: a normal subject with striatum right=1.78 and striatum left=3.05 is inconceivable even though these represent −1 standard deviation and +1 standard deviation from the normal mean respectively. Left and right values both around 1.78, or both around 3.05 are much more likely.

Table 3 of Example 2 shows calculation of the right:left ratios, showing that the variation of the ratio for the normal population is indeed much narrower than the variation of the absolute values and is independent of site and camera type. Application of correction factors or algorithms that compensate for camera type is therefore unnecessary.

Example 1 shows that the 'normal' distribution for SBR is very wide (23-24% RSD i.e. Relative Standard Deviation) and non-uniform across age groups. The ratio SBR left:SBR right is relatively narrow (4% RSD) and uniform across age groups. In an embodiments of the present invention, the left:right ratio is therefore a more sensitive tool for detecting deviation from normality. Example 3 and FIGS. 3 and 4 show that the L/R asymmetry ratio of an embodiment of the present invention is stable in the cohort of normal subjects irrespective of age, whereas the SBR method of the prior art tends to decline with age (from about 3.2 in the thirties group to about 2.2 in the eighties age group)—necessitating age corrections when data comparisons are made.

Example 4 shows that, based on SBR alone, 17 subjects were clinically 'abnormal' but were classified as normal when applying the SBR rules from the normal database. The result is low sensitivity. Only 2 clinically normal cases were wrongly classified as abnormal by the SBR method.

Example 5 shows that, when the method of the present invention is used, the number of wrongly classified clinically abnormal cases reduces from 17 to 5, i.e. 12 subjects had a changed classification as a result of involving the asymmetry determination. That is a significant improvement in the correlation of the clinical and imaging classifications. The use of the asymmetry index also classifies some clinically 'normal' cases as 'abnormal', hence reducing specificity. In that regard, the clinical standard of truth is not perfect, especially e.g. for subjects that may be converting to disease but do not as yet show any clinically abnormal symptoms. Hence, it is possible that the abnormal DaTSCAN result is an early indicator of future abnormal clinical status even though these subjects do not yet show any clinical symptoms.

ABBREVIATIONS

AD: Alzheimer's disease;
AD-HD: attention deficit hyperactivity disorder;
AOI: area of interest;
DaT: dopamine transporter;
DLB: Lewy body dementia;
DOPA: L-3,4-dihydroxyphenylalanine;
ET: essential tremor;
MSA: Multiple System Atrophy;
NDB: Normal Database;
PET: positron emission tomography;
PD: Parkinson's disease;
PS: Parkinsonian syndromes;
PSP: Progressive Supranuclear Palsy (PSP);
RSD: Relative Standard Deviation, i.e. the standard deviation expressed as a percentage of the average, RSD=(SD/Mean)×100%;
SAI: striatal asymmetry index;
SBR: striatum binding ratio;
SD: standard deviation;
SPECT: single photon emission tomography;
VMAT2: vesicular monoamine transporter type 2;
VOL volume of interest.

Example 1

Striatal Binding Ratios: Normal Range

Comparative Example

The European Association of Nuclear Medicine RESEARCH4LIFE© initiative ("EARL") has been compiling a database of DaTSCAN images of normal human subjects since 2007 (see http://earl.eanm.org/cms/website.php?id=/en/projects/enc-dat.htm). The ENCDAT database includes 150 normal subjects—with data from a range of camera types. SBR was calculated for the 150 normal subjects (Group A):

$$SBR = \frac{(\text{count density target } ROI - \text{count density reference } ROI)}{\text{count density reference } ROI}$$

where:
SBR=specific binding ratio or striatum binding ratio,
ROI=region of interest.

Brain imaging data for n=37 normal subjects acquired on GE cameras in the ENCDAT database was used for the calculation of SBR (Group B). SBR for an illustrative patient from the ENCDAT database is also shown:

TABLE 1

|  | SBR Striatum right | SBR Striatum left |
| --- | --- | --- |
| Normal A (±1 SD) | 2.88 ± 0.65 | 2.88 ± 0.69 |
| Normal B (±1 SD) | 2.41 +/− 0.63 | 2.42 +/− 0.63 |

FIG. 1 shows the variation of SBR with age for the normal patient group in the ENCDAT data set. The 95% confidence interval is shown, and can be seen to be wide.

Example 2

Striatal Left/Right Binding Ratio

Using the method of the present invention, the data from Example 1 was used to calculate a striatum right:left ratio:

TABLE 2

|  | SBR right | SBR left | Striatum Right:left |
| --- | --- | --- | --- |
| Normal (+/−1 SD) | 2.88 +/− 0.65 | 2.88 +/− 0.69 | 1.00 +/− 0.04 |
| Normal range (+/−1 SD) | 1.78-3.04 | 1.79-3.05 | 0.96-1.04 |

Table 3 below uses SBR data for normal subjects from the ENC DAT database. Three subjects from each of five different sites are shown, but the overall average is based on data from 11 sites:

TABLE 3

| Site | SBR Striatum R | SBR Striatum L | Striatum R:L ratio | Caudate R:L ratio | Putamen R:L ratio | Anterior putamen R:L ratio | Posterior Putamen R:L ratio |
| --- | --- | --- | --- | --- | --- | --- | --- |
| 1 | 4.93 | 4.79 | 1.03 | 1.01 | 1.04 | 1.01 | 1.11 |
|  | 3.23 | 3.22 | 1.00 | 1.03 | 0.99 | 0.96 | 1.07 |
|  | 3.15 | 3.09 | 1.02 | 1.05 | 1.00 | 1.00 | 0.93 |
| 2 | 3.29 | 3.25 | 1.01 | 0.98 | 1.03 | 1.03 | 1.03 |
|  | 2.65 | 2.58 | 1.03 | 1.02 | 1.02 | 1.00 | 1.08 |
|  | 3.16 | 3.11 | 1.02 | 0.97 | 1.04 | 1.00 | 1.18 |
| 3 | 2.74 | 2.60 | 1.05 | 1.05 | 1.05 | 1.00 | 1.18 |
|  | 2.69 | 2.94 | 0.92 | 0.89 | 0.93 | 0.91 | 1.00 |
|  | 1.91 | 1.88 | 1.02 | 1.03 | 1.00 | 0.98 | 1.05 |
| 4 | 4.06 | 4.03 | 1.01 | 1.05 | 0.98 | 0.97 | 0.99 |
|  | 2.56 | 2.33 | 1.10 | 1.15 | 1.06 | 1.01 | 1.20 |
|  | 3.57 | 3.28 | 1.09 | 1.11 | 1.07 | 1.06 | 1.07 |
| 5 | 2.70 | 2.62 | 1.03 | 1.07 | 1.00 | 0.99 | 1.02 |
|  | 2.37 | 2.37 | 1.00 | 0.94 | 1.03 | 1.01 | 1.07 |
|  | 2.62 | 2.50 | 1.05 | 1.03 | 1.05 | 1.03 | 1.11 |
| WHOLE mean | 2.88 | 2.88 | 1.00 | 0.99 | 1.01 | 1.00 | 1.01 |
| WHOLE Std dev. | 0.65 | 0.69 | 0.04 | 0.06 | 0.05 | 0.05 | 0.11 |
| WHOLE % RSD | 23% | 24% | 4% | 6% | 5% | 5% | 11% | where:
Site 1 = Ankara Infinia;
Site 2 = Copenhagen IRIX;
Site 3 = Genoa Varicam;
Site 4 = Leuven IRIX;
Site 5 = London Infinia;
% RSD = st dev × 100/mean.

Example 3

Normal Database (NDB)

Two databases of scans of DaTSCAN™ (GE Healthcare Ltd) normal human subjects were evaluated using:
  (i) the SBR method of the prior art (see Example 1), with the occipital cortex as the reference region;
  (ii) the L/R ratio method of the present invention.

The PPMI database was of 122 subjects (age range 31-84; 62% male 38% female). The ENCDAT database was of 122 subjects (age range 20-82; 52% male 48% female).

The data from all subjects in each decade of life (20 s, 30 s etc) were averaged. The results are shown in FIGS. 3 and 4.

Example 4

Patient Classification Using NID and SBR

Comparative Example

The data from two GE Healthcare Ltd clinical trials of Datscan™:
  (i) comparing PD and ET;
  (ii) clinically uncertain PD;

104 patients in total were analysed using SBR calculation only. Each determination was compared with the patient determination based on clinical symptoms. The results are shown in Table 4:

TABLE 4

|  |  | Clinical | | |
| --- | --- | --- | --- | --- |
|  |  | Abnormal | Normal | Total |
| SBR | Abnormal | 42 | 2 | 44 |
|  | Normal | 17 | 43 | 60 |
|  | Total | 59 | 45 | 104 |

Thus, 42 subjects (of the 104) were found to be abnormal on both SBR and clinical criteria, and 43 normal on both criteria. 17 subjects were classified as clinically abnormal, but those same subjects were categorised as normal by SBR. Two subjects were classified as normal on clinical criteria, but those same two subjects were found abnormal on SBR.

This gives a sensitivity of 71%, specificity of 96% and accuracy of 82% for the SBR technique. The clinical diagnosis was assumed to be the 'true' diagnosis, and sensitivity and specificity can then be calculated. Sensitivity=100×True Positives/(True Positives+False Negatives)=100×42/59=71%. Specificity=100×True Negatives/(True Negatives+False Positives)=100×43/45=96%.

Accuracy=100×(True Positives+True Negatives)/Population=100×(42+43)/104=82%.

Example 5

Patient Classification Using NID and L/R Ratio

The 104 patient data set from Example 4 was analysed using SBR together with the L/R asymmetry of the present invention. The results are given in Table 5:

TABLE 5

|  |  | Clinical | | |
| --- | --- | --- | --- | --- |
|  |  | Abnormal | Normal | Total |
| SBR + Asymmetry | Abnormal | 54 | 11 | 65 |
|  | Normal | 5 | 34 | 39 |
|  | Total | 59 | 45 | 104 |

This gives a sensitivity of 92%, specificity of 76% and accuracy of 85% for the SBR plus asymmetry.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A computer-implemented method useful in the diagnosis of a neurological disease, which comprises:
   (i) obtaining a dopamine transporter radiopharmaceutical image data of a subject previously administered with a radiopharmaceutical suitable for imaging a dopamine function, wherein the obtaining includes determining the uptake of said radiopharmaceutical in an equivalent region of a left and a right striatum of a brain of said subject;
   (ii) determining a value indicative of the ratio of the uptake in the equivalent left and right striatum region from the image data from step (i), wherein the ratio is calculated by dividing the uptake in the left striatum region by the uptake in the right striatum region or by dividing the uptake in the right striatum region by the uptake in the left striatum region, wherein the equivalent left and right striatum regions are regions of either the same volume (for 3-dimensional imaging) or the same area (for 2 dimensional imaging), on the left and right side of the brain; and
   (iii) comparing the ratio determined in step (ii) with a range of normal subject ratios, wherein the subject is classified as suffering from a neurological disease when the ratio from step (ii) is outside of the range of normal subject ratios, and when the ratio in step (ii) is calculated by dividing the uptake in the left striatum region by the uptake in the right striatum region, the normal subject ratios are also calculated by dividing the uptake in the left striatum region by the uptake in the right striatum region, and when the ratio in step (ii) is calculated by dividing the uptake in the right striatum region by the uptake in the left striatum region, the normal subject ratios are also calculated by dividing the uptake in the right striatum region by the uptake in the left striatum region
   wherein the method excludes further analysis to compare the image to age-matched and/or gender-matched control images.

2. The method of claim 1, where the dopamine function is chosen from:
   L-3,4-dihydroxyphenylalanine (DOPA) decarboxylase activity;
   vesicular monoamine transporter type 2 (VMAT2) binding; or
   dopamine transporter binding.

3. The method of claim 2, where the radiopharmaceutical is a VMAT2 binding radiopharmaceutical.

4. The method of claim 3, where the VMAT2 binding radiopharmaceutical is $^{18}$F-AV-133.

5. The method of claim 4, where the radiopharmaceutical is a dopamine transporter binding radiopharmaceutical.

6. The method of claim 5, where the radiopharmaceutical comprises a tropane, and is chosen from: $^{123}$I-ioflupane, $^{18}$F-ioflupane, $^{123}$I-Altropane, $^{123}$I-PE2I, $^{11}$C-PE2I, $^{123}$I-IPT, $^{123}$I-β-CIT, $^{18}$F-β-CFT, $^{99}$mTc-TRODAT or $^{99m}$Tc-technepine.

7. The method of claim 1 where the neurological disease is suspected to be Parkinson's disease, Parkinson's syndromes or Lewy Body Dementia.

8. The method of claim 1, where the equivalent region is chosen from:
   a whole striatum;
   a caudate
   a putamen; or
   or combinations thereof.

9. The method of claim 1, where the assessing of the uptake of said radiopharmaceutical in an equivalent region of the left and right striatum of the brain of said subject and/or the calculating of the ratio of the uptake in the equivalent left and right striatum region is carried out by tomographic imaging.

10. The method of claim 1, which further comprises one or more of the following:

calculating a caudate:putamen or putamen:caudate ratio for the left and right striatum separately;

calculating a striatal binding ratio (SBR) for a left and right hemisphere;

calculating a ratio of counts in equivalent left and right regions of the brain;

comparing left:right or right:left ratios obtained in calculating the ratio of counts in equivalent left and right regions of the brain with normal values.

11. A computer-implemented method of diagnosis which comprises the method of imaging of claim 1, where the comparing of the ratio for said subject is with a database of such ratios, wherein said database contains such ratios for normal subjects;

and further comprises:

classifying said subject as having a normal presentation, when the ratio is within the normal range; and classifying a patient as suffering from a neurological disease when the ratio is outside the normal range.

12. A computer-implemented method of selecting or excluding a subject for a particular therapy of a neurological disease using the method of diagnosis of claim 11, which further comprises:

assessing an uptake of said radiopharmaceutical in an equivalent region of a left and a right striatum of a brain of a subject, the subject having been previously administered a radiopharmaceutical suitable for imaging dopamine function;

calculating a ratio of the uptake in the equivalent left and right striatum region; and, comparing the ratio for said subject with a normal range of such ratios for normal subjects.

13. A method of monitoring the efficacy of a course of therapy of a neurological disease of a subject, which comprises a method comprising:

(i) obtaining a dopamine transporter radiopharmaceutical image data of a subject previously administered with a radiopharmaceutical suitable for imaging dopamine function, wherein the obtaining includes determining the; uptake of said radiopharmaceutical in an equivalent region of a left and a right striatum of a brain of said subject;

(ii) determining a value indicative of the ratio of the uptake in the equivalent left and right striatum region from the image data from step (i), wherein the ratio is calculated by dividing the uptake in the left striatum region by the uptake in the right striatum region or by dividing the uptake in the right striatum region by the uptake in the left striatum region, wherein the equivalent left and right striatum regions are regions of either the same volume (for 3-dimensional imaging) or the same area (for 2 dimensional imaging), on the left and right side of the brain;

(iii) comparing the ratio determined in step (ii) for said subject with a normal range of such ratios for normal subjects for the subject wherein steps (i)-(iii) occur after the subject has undergone the course of therapy of the neurological disease, and when the ratio in step (ii) is calculated by dividing the uptake in the left striatum region by the uptake in the right striatum region, the normal subject ratios are also calculated by dividing the uptake in the left striatum region by the uptake in the right striatum region, and when the ratio in step (ii) is calculated by dividing the uptake in the right striatum region by the uptake in the left striatum region, the normal subject ratios are also calculated by dividing the uptake in the right striatum region by the uptake in the left striatum region; and wherein the method excludes further analysis to compare the image to age-matched and/or gender-matched control images.

14. A personal computer, a gamma camera or a PET camera comprising a software tool suitable for carrying out the method of imaging as defined in claim 1.

15. The personal computer, a gamma camera or a PET camera of claim 14, further comprising the database of ratios wherein said database contains such ratios for normal subjects.

16. The method of claim 1, wherein the method is implemented with a tomographic imaging device.

* * * * *